United States Patent [19]
Shu et al.

[11] Patent Number: 5,962,662
[45] Date of Patent: Oct. 5, 1999

[54] METHOD FOR PRODUCING A FLAVORFUL AND AROMATIC COMPOSITION FOR USE IN SMOKING ARTICLES

[75] Inventors: Chi-Kuen Shu, Pfafftown; Brian Michael Lawrence, Winston-Salem, both of N.C.

[73] Assignee: R.J. Reynolds Tobacco Company, Winston-Salem, N.C.

[21] Appl. No.: 07/854,122

[22] Filed: Mar. 19, 1992

Related U.S. Application Data

[63] Continuation-in-part of application No. 07/632,242, Dec. 20, 1990, abandoned.

[51] Int. Cl.$^6$ ............... C07H 5/04; C07H 1/00; C07G 17/00
[52] U.S. Cl. ............ 536/18.7; 536/1.1; 536/124; 514/23; 514/24
[58] Field of Search ............... 536/18.7, 1.1, 536/124; 514/23, 24; 131/359, 276, 278

[56] References Cited

U.S. PATENT DOCUMENTS

| | | | |
|---|---|---|---|
| Re. 32,095 | 3/1986 | Wu et al. | 536/18.7 |
| 3,136,321 | 6/1964 | Davis et al. | 131/290 |
| 3,316,919 | 5/1967 | Green et al. | 131/194 |
| 3,744,496 | 7/1973 | Rooker et al. | 131/352 |
| 3,920,026 | 11/1975 | Warfield et al. | 536/18.7 |
| 4,286,606 | 9/1981 | Swain et al. | 536/18.7 |
| 4,421,126 | 12/1983 | Gellatly | 131/298 |
| 4,481,956 | 11/1984 | Chan | 131/331 |
| 4,506,682 | 3/1985 | Muller | 131/352 |
| 4,538,627 | 9/1985 | Chan et al. | |
| 4,701,282 | 10/1987 | Chan et al. | 131/275 |
| 4,708,151 | 11/1987 | Shelar | 131/290 |
| 4,714,082 | 12/1987 | Banerjee et al. | 131/194 |
| 4,756,318 | 7/1988 | Clearman et al. | 131/352 |
| 4,793,365 | 12/1988 | Sensabaugh, Jr. et al. | 131/359 |
| 4,862,903 | 9/1989 | Green, Jr. et al. | 131/359 |
| 4,986,286 | 1/1991 | Roberts et al. | 131/290 |
| 5,056,537 | 10/1991 | Brown et al. | 131/352 |
| 5,060,669 | 10/1991 | White et al. | 131/297 |
| 5,074,319 | 12/1991 | White et al. | 131/297 |
| 5,074,320 | 12/1991 | Jones, Jr. et al. | 131/331 |
| 5,074,321 | 12/1991 | Gentry et al. | 131/352 |

FOREIGN PATENT DOCUMENTS

| | | |
|---|---|---|
| 212234 | 3/1987 | European Pat. Off. . |
| 277519 | 8/1988 | European Pat. Off. . |
| 338831 | 10/1989 | European Pat. Off. . |

OTHER PUBLICATIONS

Lane, M.J. et al., The Maillard Reaction in Foods and Nutrition, I, American Chemical Society Symp. Ser., 215, pp. 141–158 (1983).

Shu, C–K et al., Thermal Generation of Aromas, 1989 American Chemical Society Symp. Ser., 409, pp. 229–241 (1989).

*Primary Examiner*—Louise N. Leary

[57] ABSTRACT

A flavorful and aromatic composition is provided by forming a mixture of a first component in the form of at least one non-sulfur containing amino acid, non-sulfur containing amino acid analog and/or degradation product thereof and a second component in the form of at least one sugar, sugar analog and/or degradation product thereof. The first component and second component are in a molar ratio of from about 1:1 to about 60:1. The mixture is then subjected to heat treatment in a pressure controlled environment under conditions sufficient to form the flavorful and aromatic composition, e.g., a pressure of about 10 psig to about 1000 psig and a temperature of at least 100° C. The composition is useful as casing and top dressing components for tobacco laminae and cut filler, as well as for other smokable materials.

24 Claims, 11 Drawing Sheets

METHOD FOR PRODUCING A FLAVORFUL AND AROMATIC COMPOSITION FOR USE IN SMOKING ARTICLES

RELATED APPLICATION

This application is a continuation-in-part of U.S. Ser. No. 07/632,242 filed Dec. 20, 1990, now abandoned, the entirely of which is incorporated herein by reference.

BACKGROUND OF THE INVENTION

The present invention relates to providing flavorful and aromatic compositions, and in particular to processes for providing flavorful and aromatic compositions similar to those characteristic of certain tobaccos. Such compositions are useful as additives to tobacco cut filler for cigarette manufacture.

Popular smoking articles, such as cigarettes, have a substantially cylindrical rod shaped structure and include a charge of smokable material, such as shreds or strands of tobacco material (i.e., in cut filler form), surrounded by a paper wrapper, thereby forming a tobacco rod. It has become desirable to manufacture a cigarette having a cylindrical filter element aligned in an end-to-end relationship with the tobacco rod. Typically, a filter element includes cellulose acetate tow circumscribed by plug wrap, and is attached to the tobacco rod using a circumscribing tipping material. Many cigarettes include flavorful and aromatic compounds in order to provide certain flavor and aroma characteristics to those cigarettes.

Many types of smoking products and improved smoking articles have been proposed through the years as improvements upon, or as alternatives to, the popular smoking articles. Recently, U.S. Pat. Nos. 4,708,151 to Shelar; 4,714,082 to Banerjee et al.; 4,756,318 to Clearman et al.; and 4,793,365 to Sensabaugh, Jr. et al.; and European Patent Publication Nos. 212,234 and 277,519 propose cigarettes and pipes which comprise a fuel element, an aerosol generating means physically separate from the fuel element, and a separate mouth-end piece. Such types of smoking articles provide natural tobacco flavors to the smoker thereof by heating, rather than burning, tobacco in various forms.

Flavorful and aromatic compounds are important components of smoking articles and provide improved taste and aroma to the smoking article. Thus improved processes for providing flavor and aromatic substances and flavorable and aromatic forms of tobacco are desirable. For example, various processes for producing and using tobacco extracts, aroma oils and concentrates are proposed in U.S. Pat. Nos. 3,136,321 to Davis; 3,316,919 to Green; 3,424,171 to Rooker; 4,421,126 to Gellatly and 4,506,682 to Mueller and European Patent Publication No. 338,831 to Clapp et al.

There also has been interest in reacting amino acids and sugars to produce food flavors. For example Shu et al, *Thermal Generation of Aromas,* ACS Sym. Ser., 409, pp 229–241 (1989) proposes the thermal reaction of cystine and 2,5-dimethyl-4-hydroxy-3-(2H)-furanone to generate a meat flavor. Lane et al, *The Maillard Reaction in Foods and Nutrition, I,* ACS Sym. Ser., 215, pp 141–158 (1983) proposes the thermal reaction of various amino acids and sugars, and reports the effect thereof on the odor of the resulting mixture. U.S. Pat. No. Re. 32,095 to Wu, et al. proposes reacting sugars with ammonium hydroxide in the presence of a trace amount of an amino acid to provide flavorants suitable for use in smoking products.

It would be highly desirable to provide flavorful and aromatic compounds which compliment the flavor and aroma characteristics of smokable materials.

SUMMARY OF THE INVENTION

The present invention relates to a process for providing flavorful and aromatic compositions, and particularly flavorful and aromatic compositions similar to and complimenting those found in smokable tobacco materials. In particular, at least one non-sulfur containing amino acid, non-sulfur containing amino acid analog or degradation product thereof and at least one sugar, sugar analog, or degradation product thereof are provided. The amino acid and/or amino acid analog preferably each include at least one amide, dicarboxylic acid, alkyl and/or hydroxy alkyl group. The amino acid, amino acid analog or degradation product thereof and the sugar, sugar analog or degradation product thereof are contacted thus forming a mixture, preferably in a molar ratio of amino acid to sugar of about 1:1 to 60:1, preferably about 10:1 to 60:1, and more preferably about 20:1 to 40:1. This mixture is subjected to heat treatment in a pressure controlled environment to form a flavorful and aromatic composition.

The pressure controlled environment is provided by a pressure chamber or vessel which provides, during heat treatment, containment of the amino acid and sugar mixture such that the lighter active compounds formed (e.g., ammonia, acetaldehyde, carbonyls, etc.) are contained under conditions sufficient to generate the volatile flavor and aromatic composition. The vessel provides for heat treatment at a temperature significantly above 100° C. and at a typical pressure range of from about 10 psig to about 1,000 psig, normally from about 20 psig to about 500 psig.

The resulting flavorful and aromatic compositions include various pyrazine, pyridine or pyrazinone components and mixtures thereof which are often components of tobacco-derived flavorful and aromatic compounds. The present flavorful and aromatic compositions are useful as casing or top dressing components for tobacco laminae and cut filler, as well as for other smokable materials. Alternatively, such flavorful and aromatic compositions are useful in those types of smoking articles described in U.S. Pat. Nos. 4,708,151 to Shelar; 4,714,082 to Banerjee et al.; 4,756,318 to Clearman et al.; and 4,793,365 to Sensabaugh et al.; as well as European Patent Publication Nos. 212,234 and 277,519.

The flavorful and aromatic compositions also are useful as cigarette filter additives. For example, the flavorful and aromatic compositions can be incorporated into low density polyethylene and formed into strands, and then incorporated into cigarette filters as described in U.S. Pat. Nos. 4,281,671 to Bynre et al. and 4,862,905 to Green, Jr. et al. The flavorful and aromatic compositions also are useful as cigarette wrapper additives; or as additives to the inner regions of cigarette packages (e.g., within a paper/foil laminate of cigarette package or within a low density polyethylene film which is placed within a cigarette package) in order to provide a desirable cigarette aroma and "pack aroma."

DETAILED DESCRIPTION OF THE PREFERRED EMBODIMENTS

Figure 1:
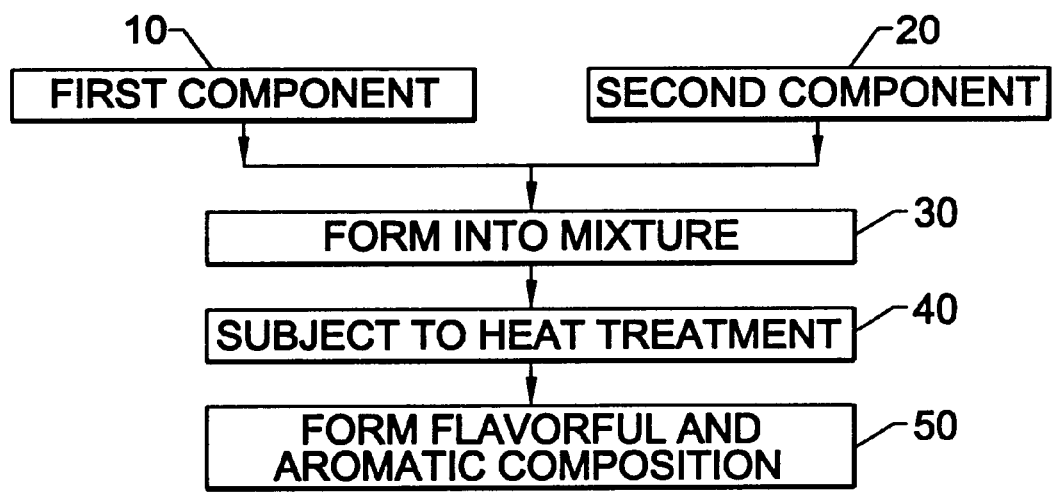
FIG. 1 is a schematic diagram of process steps of an embodiment of the present invention.

Referring to FIG. 1, a first component 10 in the form of at least one non-sulfur containing amino acid, non-sulfur containing amino acid analog and/or degradation product thereof and a second component 20 in the form of at least one sugar, sugar analog, and/or degradation product thereof are provided. The first component 10 and the second component 20 are formed into a mixture 30. The mixture 30 is subjected 40 to heat treatment in a pressure controlled environment under conditions to form the flavorful and aromatic composition 50.

Examples of suitable non-sulfur containing amino acids and/or non-sulfur containing amino acid analogs are those including at least one amide group, dicarboxylic acid group, alkyl group and/or hydroxyalkyl group. Exemplary amino acids include asparagine, glutamine, phenylalanine, threonine, aspartic acid, glutamic acid, serine, proline, hydroxyproline, and the like. Exemplary amino acid analogs include ammonia and primary amines (e.g., $RNH_2$ wherein R is $C_1$–$C_{10}$). Exemplary primary amines include ethylamine, butylamine, etc. An exemplary amino acid degradation product is the degradation product of asparagine, namely alanine amine.

Examples of suitable sugars are fructose, glucose, sucrose, rhamnose and mannose. Examples of suitable sugar analogs are 2,5-dimethyl-4-hydroxy-3-(2H)-furanone, 4,5-dimethyl-3-hydroxy-2-(5H)-furanone, maltol, and methyl-cyclopentenolone. The sugars and sugar analogs undergo degradation via a rearrangement mechanism to form α-dicarbonyl compounds such as 2,3-pentanedione, 2,3-butanedione, 3,4-hexanedione, 2,3-hexanedione, etc. Thus, α-dicarbonyls can be used directly.

The non-sulfur containing amino acid, non-sulfur containing amino acid analog and/or degradation product thereof and the sugar, sugar analog, and/or degradation product thereof are contacted and formed into a mixture, preferably in a molar ratio of from about 1:1 to 60:1, preferably from about 10:1 to 60:1, and more preferably about 20:1 to 40:1 amino acid to sugar.

The mixture is subjected to heat treatment in a pressure controlled environment sufficient to provide the flavorful and aromatic composition. Such a pressure controlled environment is provided by enclosing the amino acid/sugar mixture in an air sealed vessel or chamber. The mixture preferably is in the presence of water in an amount of at least about 5 percent by weight, normally at least about 15 percent by weight and preferably at least about 25 percent by weight on the total weight of the moist mixture. Typically, the pressure controlled environment is provided using a pressure vessel or chamber which is capable of withstanding relatively high pressures. Such vessels or chambers (i) provide enclosure or containment of the mixture such that the lighter active compounds are not lost or do not otherwise escape during the moderately high temperature treatment step, and (ii) provide for treatment of the mixture at a temperature significantly above about 100° C. so as to form the volatile flavor and aromatic compositions characteristic of certain tobaccos, e.g., the pyrazines and pyridines often found in tobacco-derived flavorful and aromatic compounds. Additionally, when asparagine or alanine amide are employed as the amino acid or degradation product thereof, flavorful and aromatic pyrazinones can be formed.

Preferred pressure vessels are equipped with an external heating source. Examples of vessels which provide a pressure controlled environment include a Reaction Vessel Model No. 250 available from Berghof/America, Inc., Concord, Calif. or a Parr Reactor Model No. 4522 available from The Parr Instrument Company equipped with a temperature control unit available as Parr Model No. 4842-PID from the Parr Instrument Co. (see, for example, U.S. Pat. No. 5,060,669 to White et al., the disclosure of which is herein incorporated by reference). Operation of such exemplary vessels will be apparent to the skilled artisan. Typical pressures experienced by the mixture during the process of the present invention range from about 10 psig to about 1,000 psig, normally from about 20 psig to about 500 psig.

The amount of time that the mixture is subjected to the temperature treatment in a pressure controlled environment can vary. Normally, the time period is sufficient to heat the entire mixture at the desired temperature for a period of at least about 10 minutes, preferably at least about 20 minutes. Normally, the time period is less than about three hours, preferably less than about one hour. However, it is desirable to control the time/temperature profile of the mixture subjected to heat treatment so that it is not subjected to a particularly high temperature for a lengthy period of time. It is highly desirable to employ a pressure vessel design or a vessel equipped with an agitation mechanism such that the particular mixture experiences a relatively uniform temperature throughout the treatment period. In particular, it is highly desirable for the entire mixture to be heated uniformly throughout as much as possible at the maximum temperature to which the mixture is subjected.

Conditions provided during the heat treatment most desirably are such that the amino acids and sugars undergo Maillard reactions or "browning reactions." See, Maillard, *Ana. Chim.*, Vol. 9, pp. 5 and 258 (1916); Hodge, *J. Agric. Food Chem.*, Vol. 1, p. 928 (1953); Nursten, *Food Chem.*, Vol. 6, p. 263 (1981) and Waller et al., *ACS Symp. Ser.* (1983). Such reactions result in a significant darkening of the mixture. Additionally, flavoring agents (e.g., cocoa, licorice, St. John's bread, spices, herbs, and the like) can be added to the mixture to further enhance the flavor and aromatic characteristics of the resulting composition.

The collected flavorful and aromatic composition is used in various forms in the manufacture of smoking articles. For example, the flavorful and aromatic composition can be used as casing and top dressing components for various smokable materials. The flavorful and aromatic composition also can be contacted with tobacco and employed as a form of tobacco in smoking article manufacture. For example, tobacco cut filler, as well as the types of smokable materials described in U.S. patent application Ser. No. 276,161, filed Nov. 23, 1988, can be coated or otherwise contacted with about 0.001 to about 1 percent by weight of the flavorful and aromatic composition, based on the weight of the particular smokable material. Furthermore, the coated tobacco cut filler may be combined with aerosol forming materials, and employed in the manufacture of those smoking articles described in U.S. Pat. Nos. 4,708,151 to Shelar; 4,771,795 to White et al.; 4,714,082 to Banerjee et al.; 4,756,318 to Clearman et al.; and 4,793,365 to Sensabaugh et al.; as well as European Patent Publication Nos. 212,234 and 277,519. In addition, the coated tobacco cut filler can be incorporated into those smoking articles described in U.S. patent application Ser. No. 5,074,321 to White et al. and European Patent Publication No. 280,990.

The flavorful and aromatic composition can also be contacted with a substrate. Preferred substrates are normally solid materials and are thermally stable at those temperatures experienced during the heat treatment steps of the present invention. Examples of suitable substrate materials include porous carbons, carbon fibers, carbon yarns, high surface area glass beads, aluminas, clays, and the like. Typical substrates are aluminas available as D-2 Sintered Alpha Alumina from W. R. Grace & Co. and carbon yarns available as Kynol Catalogue No. CFY-020Y-3 from American Kynol, Inc.

The following Examples are provided in order to further illustrate various embodiments of the invention but should not be construed as limiting the scope thereof. Unless otherwise noted, all parts and percentages are by weight.

COMPARATIVE EXAMPLE 1

Figure 2:
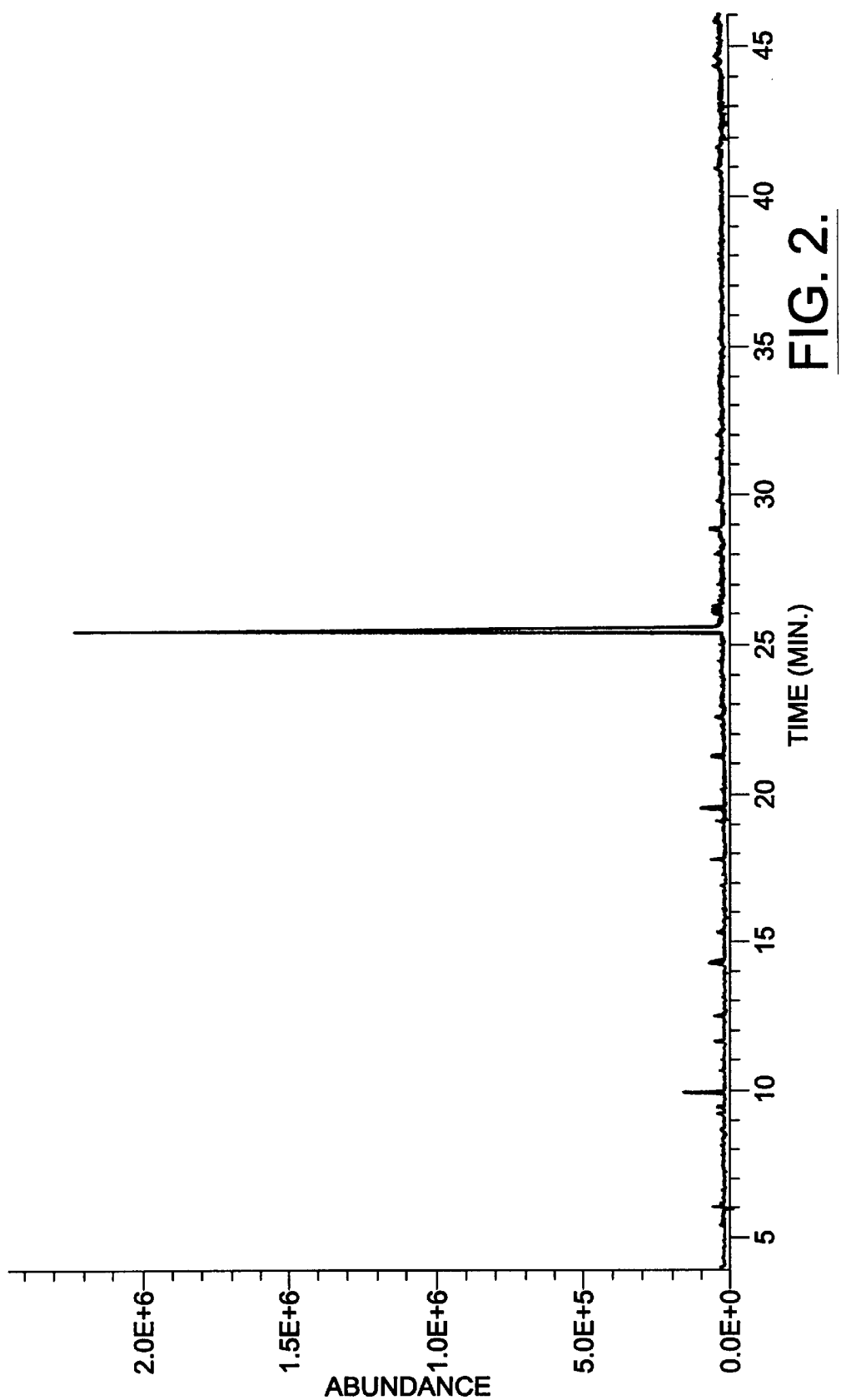
FIGS. 2–4 are gas chromatograms corresponding to Comparative Examples 1–3.

A 6.6 g sample of asparagine in the presence of 100 ml of water is reacted in a Berghof/America Inc. Reaction Vessel Model No. 250 equipped with a temperature control unit. The pressure vessel is equipped with a mechanical stirrer. The asparagine then is subjected to exposure to a maximum temperature of about 200° C. for about 60 minutes at a pressure of about 300 psig. Then, the composition is removed from the pressure vessel. Gas chromatography is performed using a fused silica DBWAX column 30 m×0.32 mm ID at 50° to 188° C. at 6° C./min available from J&W Scientific Inc., Rancho Cordova, Calif. The resulting chromatogram is shown in FIG. 2. Only peaks characteristic of a major portion of dimethyl maleimide and a minor portion of ethyl methyl pyridine can be identified from the chromatogram. This indicates that the desired pyrazines and pyridines are not formed in sufficient amounts to result in a flavorful and aromatic composition.

COMPARATIVE EXAMPLE 2

Figure 3:
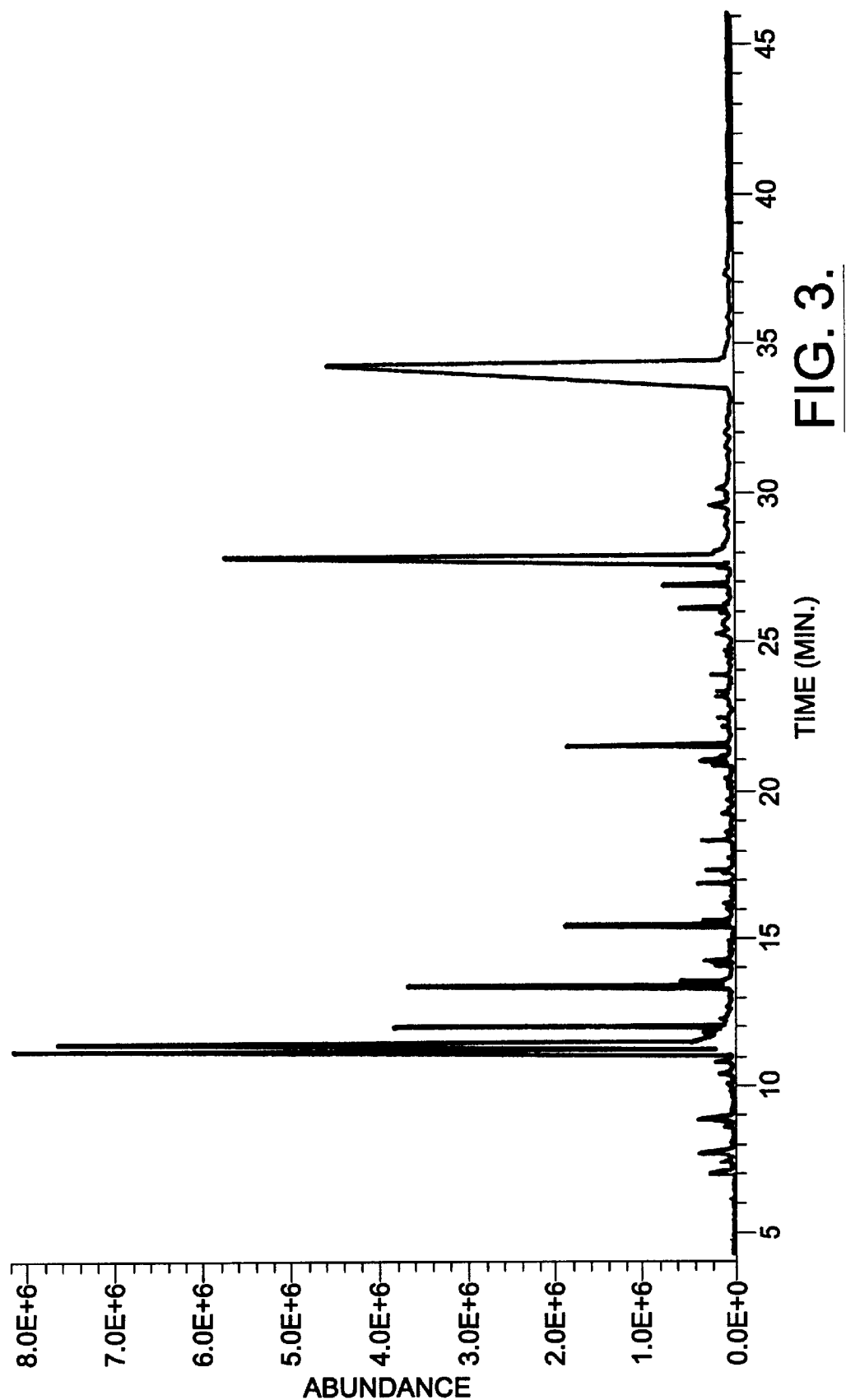

A 9.0 g sample of fructose in the presence of 100 ml of water is reacted under the same conditions as in Comparative Example 1. The gas chromatogram is shown in FIG. 3. Peaks characteristic of a large portion of furans and furfurals can be identified from the chromatogram; however, the reaction of a sugar alone does not appear to provide for the formation of the desired pyrazine and pyridine peaks characteristic of the flavorful and aromatic composition.

COMPARATIVE EXAMPLE 3

Figure 4:
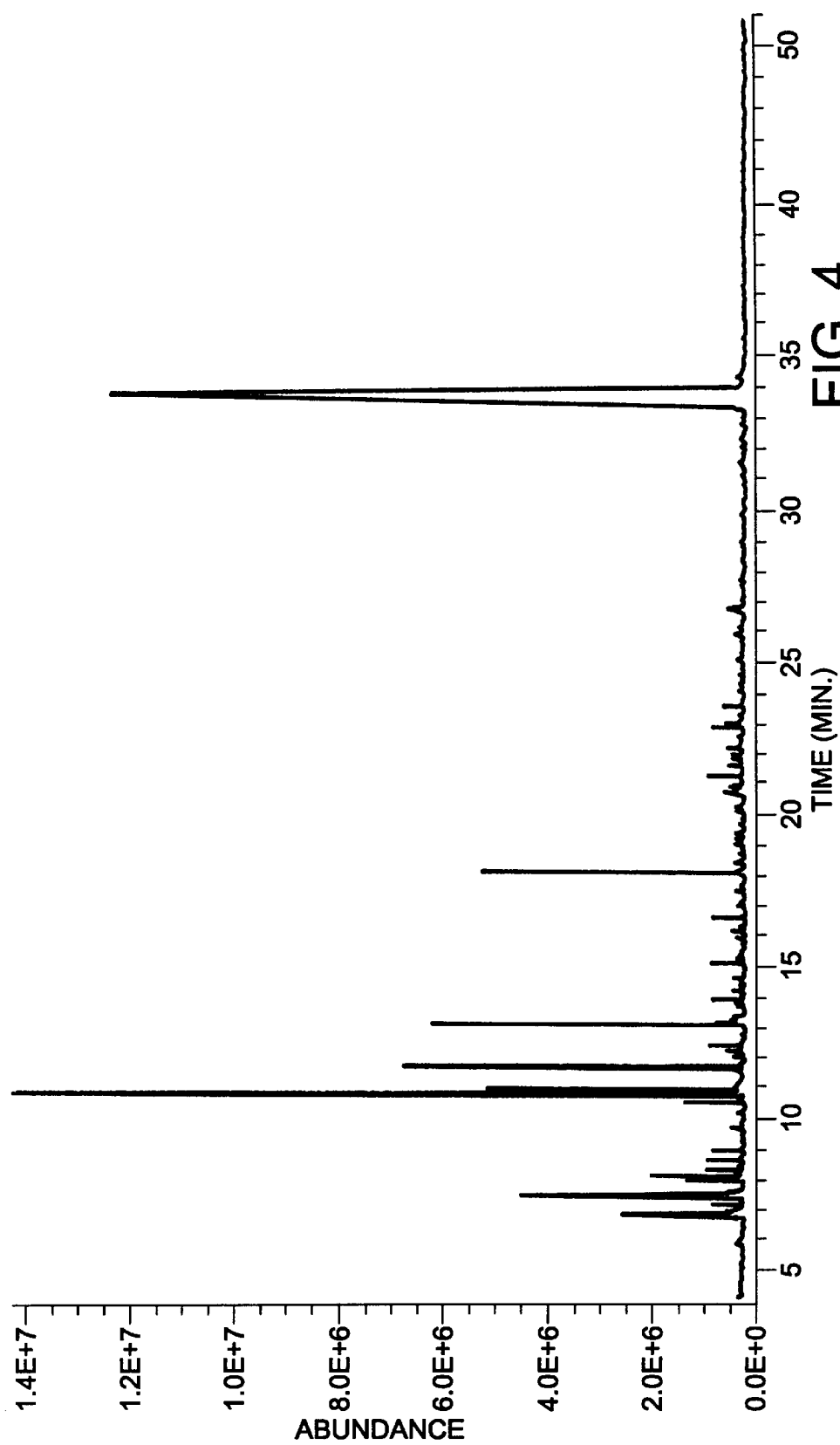

A mixture of 0.66 g of asparagine and 9.0 g of fructose (e.g., a molar ratio of 1:10 amino acid to sugar) in the presence of 100 ml of water is reacted under the same conditions as in Comparative Example 1. The gas chromatogram is shown in FIG. 4. Various furans and furfurals can be identified from the peaks of the chromatogram. The peaks, however, only indicate the presence of small amounts of pyrazines and pyridines. The amount thereof is insufficient to provide a flavorful and aromatic composition suitable for use with smokable materials.

EXAMPLE 1

Figure 5:
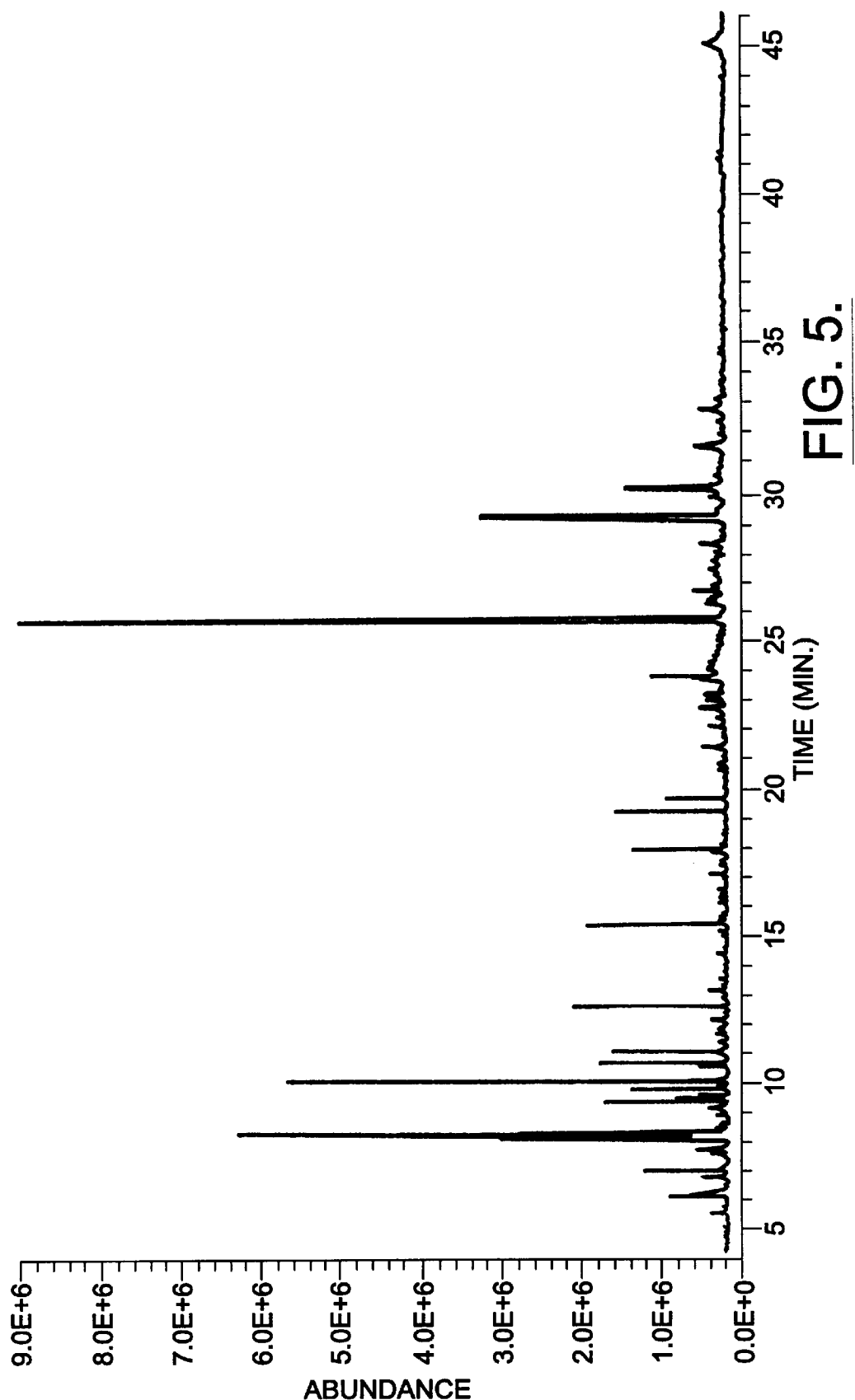
FIGS. 5–11 are gas chromatograms corresponding to Examples 1–7 and illustrate the peaks characteristic of flavorful and aromatic compositions produced according to Examples 1–7.

A mixture of 26.0 g of asparagine and 0.9 g of fructose (e.g., a molar ratio of 40:1 amino acid to sugar) in the presence of 100 ml of water is reacted under the same conditions as in Comparative Example 1. The gas chromatogram of the resulting composition is shown in FIG. 5. The peaks characteristic of various pyridines such as pyridine, 2-methyl pyridine, 2,6-dimethyl pyridine, 3-methyl pyridine, 4-methyl pyridine, 2,4-dimethyl pyridine, 2,3-dimethyl pyridine, 2,4,6-trimethyl pyridine, 3-ethyl pyridine, ethyl-methyl pyridine, and dimethyl-ethyl pyridine, and various pyrazines such as methyl pyrazine, 2,5-dimethyl pyrazine, 2,6-dimethyl pyrazine, 2-ethyl-5-methyl pyrazine, 2-ethyl-6-methyl pyrazine, trimethyl pyrazine, dimethyl-ethyl pyrazine and diethyl-methyl pyrazine can be identified from the peaks of the chromatogram. This indicates that a flavorful and aromatic composition has been formed. Many of these peaks are not evident in the gas chromatograms of Comparative Examples 1–3 which are shown in FIGS. 2–4.

EXAMPLE 2

Figure 6:
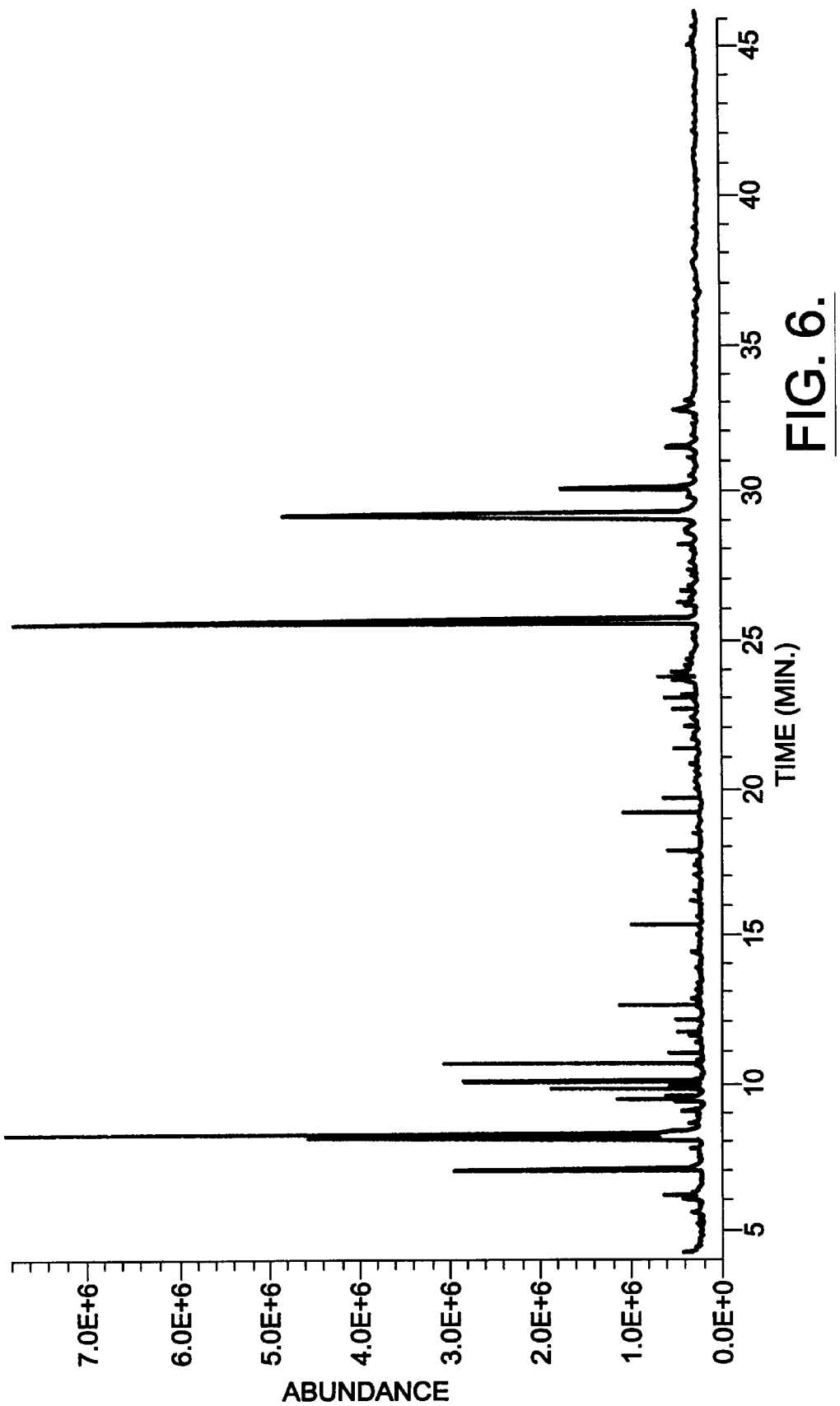

A mixture of 13.2 g of asparagine and 0.9 g of fructose (e.g., a molar ratio of 20:1 amino acid to sugar) in the presence of 100 ml of water is reacted under the same conditions as in Comparative Example 1. The gas chromatogram of the resulting mixture is shown in FIG. 6 and the peaks of the chromatogram characteristic of various pyrazines and pyridines, i.e., those formed in Example 1, can be identified, thus indicating the formation of a flavorful and aromatic composition. Many of these peaks are not evident in the gas chromatograms of Comparative Examples 1–3 which are shown in FIGS. 2–4.

EXAMPLE 3

Figure 7:
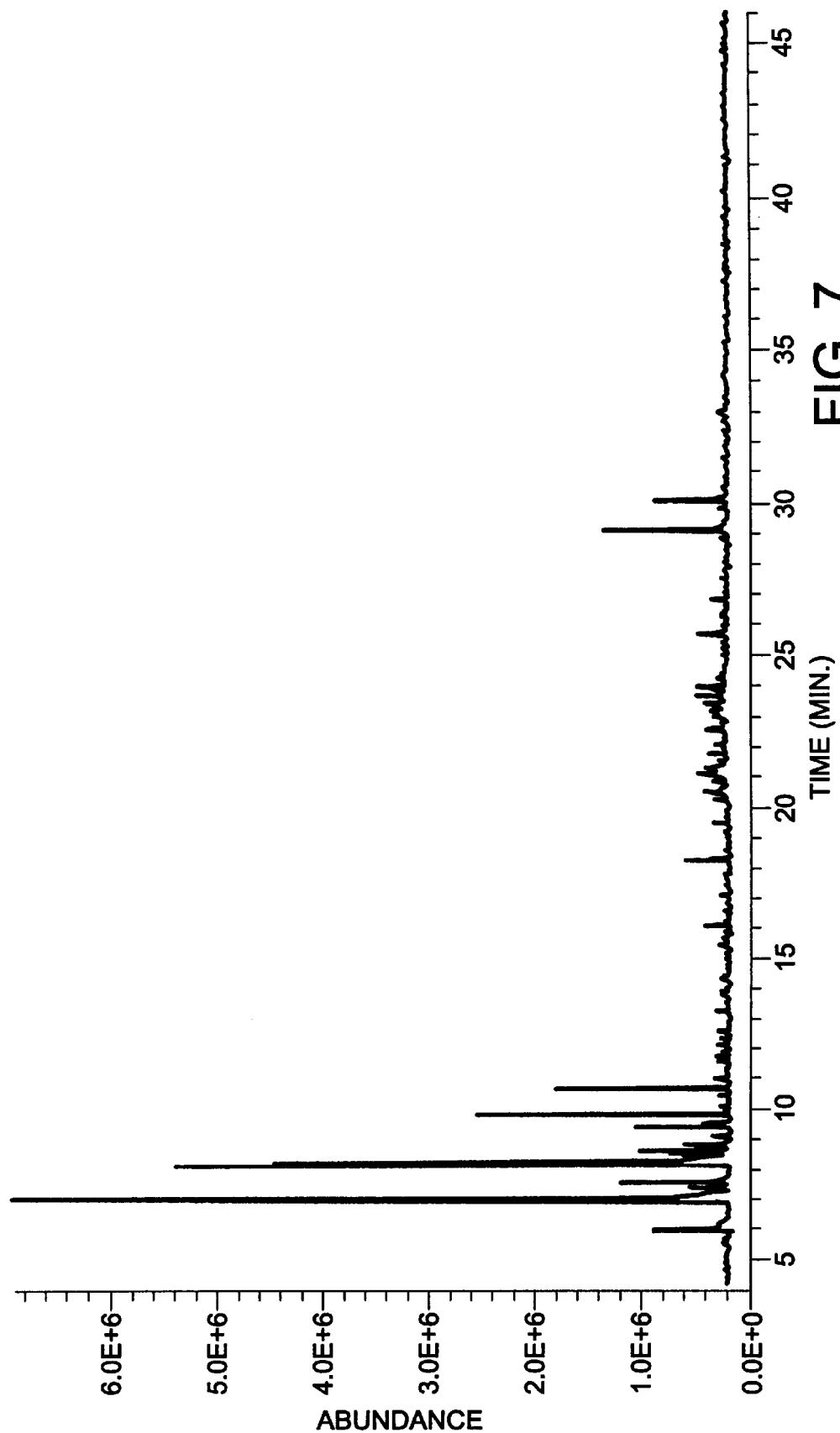

A mixture of 0.66 g of asparagine and 0.9 g of fructose (e.g., a molar ratio of 1:1 amino acid to sugar) in the presence of 100 ml of water is reacted under the same conditions as in Example 1. The gas chromatogram is shown in FIG. 7 and indicates the peaks characteristic of the various pyrazines and pyridines of the desired flavorful and aromatic composition. Many of these peaks are not evident in the gas chromatograms of Comparative Examples 1–3 which are shown in FIGS. 2–4.

EXAMPLE 4

Figure 8:
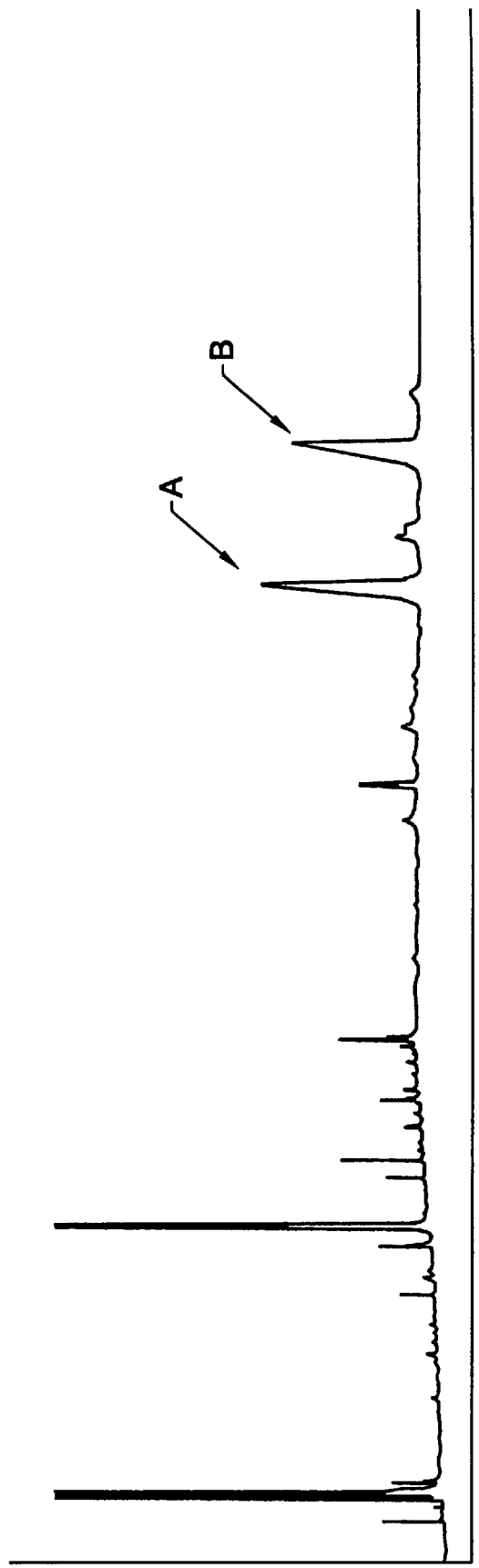

A mixture of 61.0 g of asparagine and 1 g of 2,3-pentanedione (e.g., a molar ratio of 5:1 amino acid to 2,3-pentanedione) in the presence of 50 ml is reacted under the same conditions as in Comparative Example 1. Gas chromatography is performed using a glass capillary Supelcowax 10 30 mm×0.75 ID at 50° to 188° C. at 6° C./min available from Supelco Inc., Bellefonte, Pa. The gas chromatogram of the resulting mixture is shown in FIG. 8 and indicates the peaks characteristic of the various pyrazines, pyridines and pyrazinones of the desired flavorful and aromatic composition. Peaks indicative of a major portion of the isomers, 3,5-dimethyl-2(1H)-6-propyl-pyrazinone and 3,6-dimethyl-5-propyl-2(1H)-pyrazinone, are evident and are designated in FIG. 8 as A and B. Many of the pyrazine, pyridine and pyrazinone peaks are not evident in the gas chromatograms of Comparative Examples 1–3 which are shown in FIGS. 2–4.

EXAMPLE 5

Figure 9:
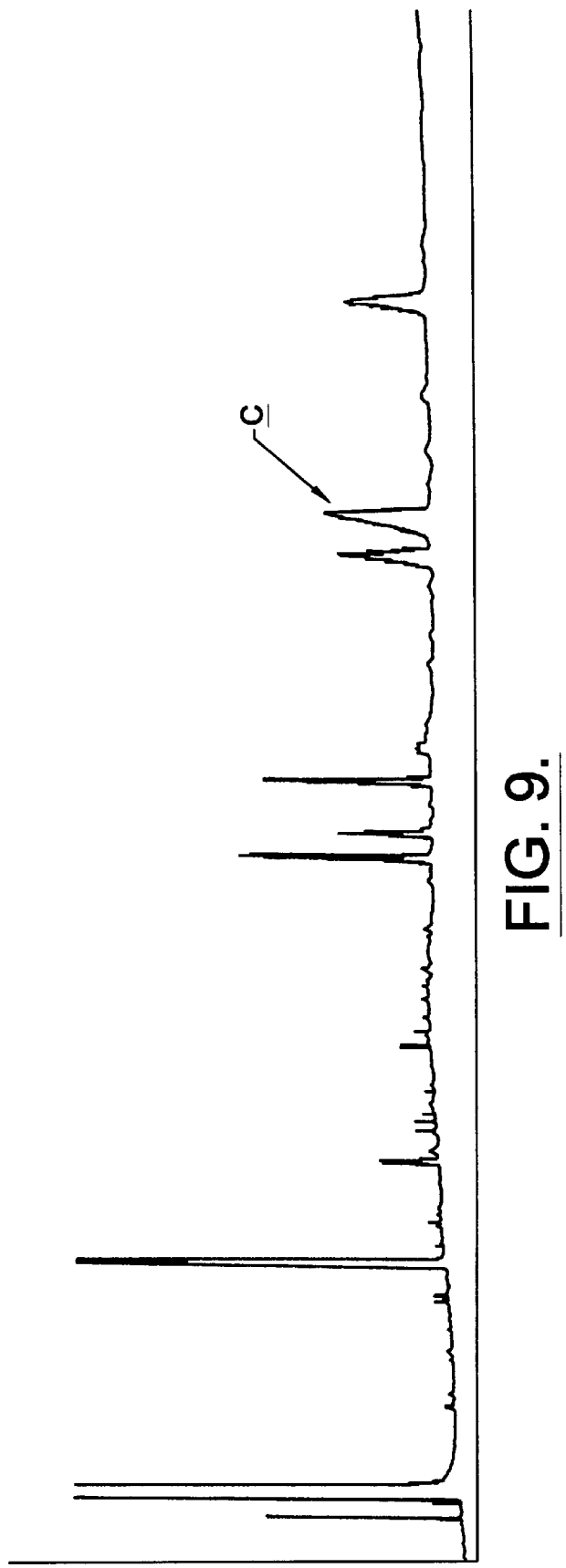

Example 4 is repeated except 1.3 g of 2,3-butanedione is used instead of 2,3-pentanedione. The gas chromatogram of the resulting mixture is shown in FIG. 9 and indicates the peaks characteristic of the various pyrazines, pyridines and pyrazinones of the desired flavorful and aromatic composition. Many of these peaks are not evident in the gas chromatograms of Comparative Examples 1–3. Particularly, a peak, designated as C, indicative of a major portion of 3,5,6-trimethyl-2(1H)-pyrazinone, is also evident.

EXAMPLE 6

Figure 10:

Example 4 is repeated except 1.3 g of 3,4-hexanedione is used instead of 2,3-pentanedione. The gas chromatogram of the resulting mixture is shown in FIG. 10 and indicates the peaks characteristic of the various pyrazines, pyridines and pyrazinones of the desired flavorful and aromatic composition. Many of these peaks are not evident in the gas chromatograms of Comparative Examples 1–3. Particularly, a peak, designated as D, indicative of a major portion of 3-methyl-5,6-diethyl-2(1H)-pyrazinone is evident.

EXAMPLE 7

Figure 11:
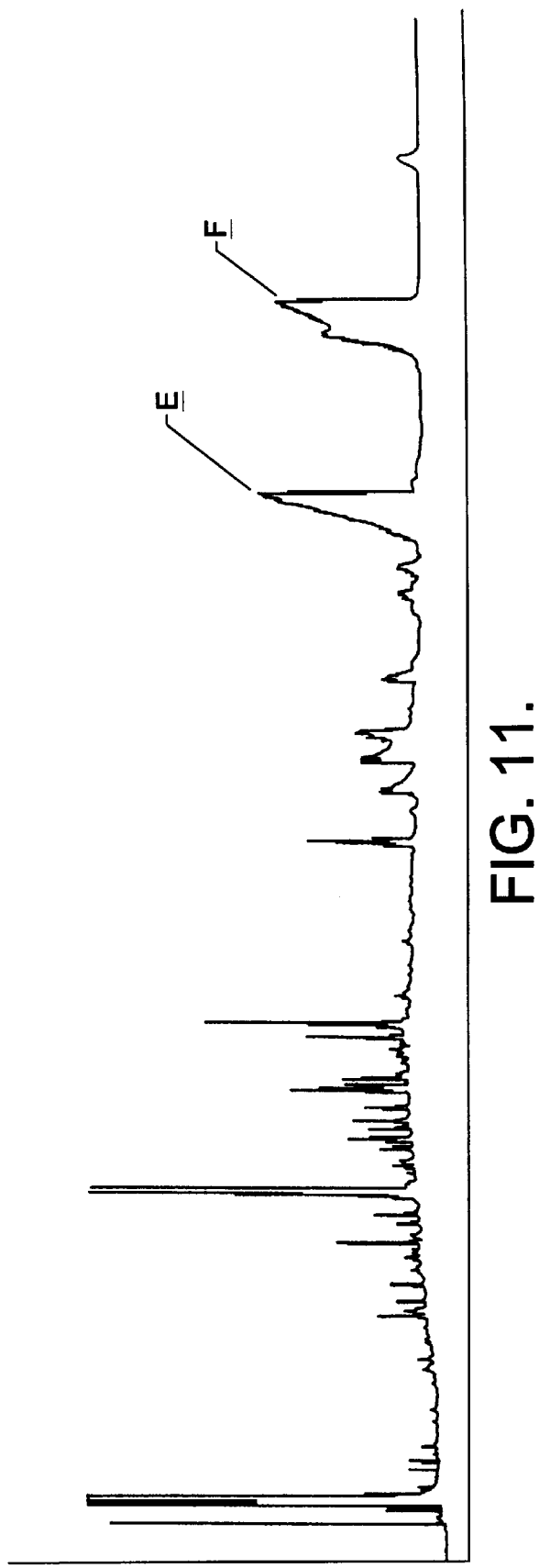

Example 4 is repeated except 1.3 g of 2,3-hexanedione is used instead of 2,3-pentanedione. The gas chromatogram of the resulting mixture is shown in FIG. 11 and indicates the peaks characteristic of the various pyrazines, pyridines and pyrazinones of the desired flavorful and aromatic composition. Many of these peaks are not evident in the gas chromatograms of Comparative Examples 1–3. Particularly, peaks designated as E and F, indicative of the isomers, 3,5-dimethyl-6-propyl-2(1H)-pyrazinone and 3,6-dimethyl-5-propyl-2(1H)-pyrazinone, are evident.

EXAMPLE 8

The collected flavorful and aromatic mixture of Example 2 is applied to an "American" blend of tobacco cut filler. In particular, 0.1% by weight of collected composition based on the weight of the tobacco cut filler is contacted with ethanol and injected into a tobacco rod such that there is 1 ppm of composition based on the weight of cut filler in the rod to a cigarette is formed from the tobacco rod, and is aged at room temperature for about two weeks. The cigarette, when smoked, exhibits a smoke perceived as smooth with good tobacco taste. The smoke has a good aroma and enhanced flavor during smoking.

EXAMPLE 9

The collected flavorful and aromatic composition of Example 4 is applied to an "American" blend of tobacco cut filler. In particular, 0.1% by weight of collected composition based on the weight of the tobacco cut filler is contacted with ethanol and injected into a tobacco rod such that there is 1 ppm of composition based on the weight of cut filler in the rod to a cigarette is formed from the tobacco rod, and is aged at room temperature for about two weeks. The cigarette, when smoked, exhibits a smoke perceived as smooth with good tobacco taste. The smoke has a good aroma and enhanced flavor during smoking.

That which we claim is:

1. A process for providing a flavorful and aromatic composition comprising the steps of:
    (a) providing a first component in the form of at least one non-sulfur containing amino acid, non-sulfur containing amino acid analog and/or degradation product thereof;
    (b) providing a second component in the form of at least one sugar, sugar analog and/or degradation product thereof;
    (c) forming a mixture of the first component and the second component whereby the molar ratio of the first component to the second component ranges from about 1:1 to about 60:1; and
    (d) subjecting the mixture of step (c) to heat treatment in a pressure controlled environment under conditions sufficient to form the flavorful and aromatic composition.

2. The process according to claim 1 whereby the molar ratio of the first component to the second component is from about 20:1 to about 40:1.

3. The process according to claim 1 whereby the heat treatment in a pressure controlled environment sufficient to form the flavorful composition includes a pressure of about 10 psig to about 1000 psig and a temperature of at least 100° C.

4. The process according to claim 1 or 2 whereby the mixture includes at least about 5 percent by weight water based on the total weight of mixture.

5. The process according to claim 1 or 2 wherein the first component is an amino acid including at least one amide, dicarboxylic acid, alkyl and/or hydroxy alkyl group.

6. The process according to claim 1 or 2 wherein the second component is a sugar selected from the group consisting of fructose, glucose, sucrose, mannose or a sugar analog selected from the group consisting of 2,5-dimethyl-4-hydroxy-3-(2H)-furanone, 4,5-dimethyl-3-hydroxy-2-(5H)-furanone, maltol, and methylcyclopentenolone.

7. The process according to claim 1 or 2 whereby the second component includes a α-dicarbonyl degradation product.

8. The process according to claim 7 whereby the α-dicarbonyl degradation product is selected from the group consisting of 2,3-pentanedione, 2,3-butanedione, 3,4-hexanedione and 2,3-hexanedione.

9. The process according to claim 1 or 2 wherein the first component includes asparagine and the second component includes fructose or the degradation product thereof.

10. A process for providing a flavorful and aromatic composition comprising the steps of:
    (a) providing a first component in the form of at least one non-sulfur containing amino acid, non-sulfur containing amino acid analog and/or degradation product thereof;
    (b) providing a second component in the form of at least one sugar, sugar analog and/or degradation product thereof;
    (c) forming a mixture of the first component and the second component whereby the molar ratio of the first component to the second component ranges from about 10:1 to about 60:1; and
    (d) subjecting the mixture of step (c) to heat treatment in a pressure controlled environment at a pressure of about 10 psig to about 1000 psig and a temperature of at least 100° C. under conditions sufficient to form the flavorful and aromatic composition.

11. The process according to claim 10 whereby the molar ratio of the first component to the second component is from about 20:1 to about 40:1.

12. The process according to claim 10 or 11 whereby the mixture includes at least about 5 percent by weight water based on the total weight of mixture.

13. The process according to claim 10 or 11 wherein the first component is an amino acid including at least one amide, dicarboxylic acid, alkyl and/or hydroxy alkyl group.

14. A process according to claim 10 or 11 wherein the second component is a sugar selected from the group consisting of fructose, glucose, sucrose and mannose or a sugar analog selected from the group consisting of 5-dimethyl-4-hydroxy-3-(2H)-furanone, 4,5-dimethyl-3-hydroxy-2-(5H)-furanone, maltol and methylcyclopentenolone.

15. The process according to claim 10 or 11 whereby the second component includes an α-dicarbonyl degradation product.

16. The process according to claim 15 whereby the α-dicarbonyl degradation product is selected from the group consisting of 2,3-pentanedione, 2,3-butanedione, 3,4-hexanedione and 2,3-hexanedione.

17. The process according to claim 10 or 11 wherein the first component includes asparagine and the second component includes fructose.

18. A process for providing a flavorful and aromatic composition comprising the steps of:
    (a) providing a first component in the form of asparagine or alanine amide;

(b) providing a second component in the form of at least one sugar, sugar analog and/or degradation product thereof;

(c) forming a mixture of the first component and the second component whereby the molar ratio of the first component to the second component ranges from about 1:1 to about 60:1; and (d) subjecting the mixture of step (c) to heat treatment in a pressure controlled environment under conditions sufficient to form the flavorful and aromatic composition.

19. The process according to claim 18 whereby the molar ratio of the first component to the second component is from about 20:1 to about 40:1.

20. The process according to claim 18 or 19 whereby the heat treatment in a pressure controlled environment sufficient to form the flavorful composition includes a pressure of about 10 psig to about 1000 psig and a temperature of at least 100° C.

21. The process according to claim 18 or 19 whereby the mixture includes at least about 5 percent by weight water based on the total weight of mixture.

22. The process according to claim 18 or 19 wherein the second component is a sugar selected from the group consisting of fructose, glucose, sucrose and mannose or a sugar analog selected from the group consisting of 5-dimethyl-4-hydroxy-3-(2H)-furanone, 4,5-dimethyl-3-hydroxy-2-(5H)-furanone, maltol and methylcyclopentenolone.

23. The process according to claim 18 or 19 whereby the second component includes an $\alpha$-dicarbonyl degradation product.

24. The process according to claim 23 wherein the degradation product is selected from the group consisting of 2,3-pentanedione, 2,3-butanedione, 3,4-hexanedione, and 2,3-hexanedione.

* * * * *